United States Patent

Walter et al.

(10) Patent No.: US 9,295,530 B2
(45) Date of Patent: Mar. 29, 2016

(54) DEVICE FOR MIXING AND DISPENSING FLOWABLE COMPONENTS

(71) Applicant: 3M INNOVATIVE PROPERTIES COMPANY, St. Paul, MN (US)

(72) Inventors: Alexander Walter, Pürgen (DE); Marc Peuker, Schöndorf (DE); Andreas J. Boehm, Reichling (DE); Mathias Bertl, Wildsteig (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/384,456

(22) PCT Filed: Mar. 6, 2013

(86) PCT No.: PCT/US2013/029234
§ 371 (c)(1),
(2) Date: Sep. 11, 2014

(87) PCT Pub. No.: WO2013/142043
PCT Pub. Date: Sep. 26, 2013

(65) Prior Publication Data
US 2015/0108166 A1    Apr. 23, 2015

(30) Foreign Application Priority Data
Mar. 20, 2012 (EP) ..................................... 12160428

(51) Int. Cl.
*B67D 7/70* (2010.01)
*A61C 5/06* (2006.01)
(Continued)

(52) U.S. Cl.
CPC ............... *A61C 5/064* (2013.01); *B01F 5/0665* (2013.01); *B01F 5/0671* (2013.01); *B01F 13/0023* (2013.01); *B01F 2215/0027* (2013.01)

(58) Field of Classification Search
CPC . A61C 5/064; B01F 13/0023; B01F 13/0027; B01F 2215/0027; B01F 2215/0029; B01F 5/0665; B01F 5/0671; A61M 5/31511
USPC ......... 433/90; 222/137, 136, 132, 145.6, 129, 222/139, 386; 604/222, 228, 218, 219, 230, 604/82–92
See application file for complete search history.

(56) References Cited

U.S. PATENT DOCUMENTS

| 1,097,474 A | 5/1914 | Schroeder |
| 1,925,786 A | 9/1933 | Brooks |

(Continued)

FOREIGN PATENT DOCUMENTS

| EP | 0232733 | 8/1987 |
| EP | 1091798 | 4/2001 |

(Continued)

OTHER PUBLICATIONS

International Search Report for PCT International Application No. PCT/US2013/029234, mailed on Apr. 26, 2013, 4 pages.

*Primary Examiner* — Lien Ngo

(57) ABSTRACT

A device for mixing and dispensing at least two flowable components comprises a housing front face with an outlet for the components and a piston having a piston front face. The piston is arranged such that the piston front face and the housing front face are facing each other. The piston front face and the housing front face are adapted to form a channel for the components between each other. The device is adapted to reduce the channel upon urging the piston front face and the housing front face against each other and thereby to displace the components to flow toward the outlet. The device facilitates mixing and dispensing a multi-component dental material.

11 Claims, 3 Drawing Sheets

(51) Int. Cl.
*B01F 5/06* (2006.01)
*B01F 13/00* (2006.01)

(56) References Cited

U.S. PATENT DOCUMENTS

| | | | |
|---|---|---|---|
| 3,331,538 A * | 7/1967 | Higgins | A61M 5/31511 222/387 |
| 4,538,920 A | 9/1985 | Drake | |
| 4,599,082 A * | 7/1986 | Grimard | A61M 5/284 215/355 |
| 4,648,532 A * | 3/1987 | Green | 222/82 |
| 5,443,182 A * | 8/1995 | Tanaka et al. | 222/137 |
| 5,770,141 A * | 6/1998 | Schulte et al. | 264/311 |
| 5,795,337 A * | 8/1998 | Grimard | A61M 5/31511 604/222 |
| 5,865,798 A * | 2/1999 | Grimard | A61M 5/31596 604/218 |
| 6,319,002 B1 * | 11/2001 | Pond | 433/89 |
| 7,287,898 B2 | 10/2007 | Pauser | |
| 7,674,003 B2 | 3/2010 | Sharrah | |

FOREIGN PATENT DOCUMENTS

| | | |
|---|---|---|
| GB | 554085 | 6/1943 |
| GB | 933709 | 8/1963 |
| NL | 1608 | 11/1912 |
| WO | 00-01473 | 1/2000 |
| WO | 03-041605 | 5/2003 |

* cited by examiner

DEVICE FOR MIXING AND DISPENSING FLOWABLE COMPONENTS

FIELD OF THE INVENTION

The invention relates to a device for mixing and dispensing at least two flowable components, and in particular to a device which forms a channel between a piston and a housing of the device, with the channel being compressible for mixing and dispensing the components.

BACKGROUND ART

In dentistry there are devices for storing materials in the form of individual components which are to be mixed prior to use. Some devices include a mixer which allows for mixing the components as they are dispensed from such a package.

For example EP 0 232 733 A2 discloses a two-component dispensing device including a dispensing cartridge. The device comprises a storage space and a mixer tube. The mixer tube has mixer vanes which are arranged longitudinally in a row against one another, are twisted alternately to the left and the right and are mounted rotationally offset from one another.

U.S. Pat. No. 4,538,920 discloses a multiple-barrel dispensing device having a syringe, an exit conduit, a static mixing element, means for detachably coupling the inlet of the exit conduit to the outlet end of the syringe, and means for locating the static mixing element within the exit conduit to provide rotational alignment of the static mixing element relative to the syringe.

EP 1 368 113 A1 discloses a dynamic mixer for mixing paste components. The mixer comprises a housing with inlet openings and an outlet opening. A mixer element is rotatably mounted in a mixing chamber of the housing. The mixer element can be driven by a dispensing device for mixing the paste components within the housing.

Although existing devices for mixing components are available there is still a desire to provide a design which is easy to use and which is relatively inexpensive.

SUMMARY OF THE INVENTION

The invention relates to a device for mixing and dispensing at least two flowable components. Preferably components are adapted to be mixed to form a dental material. The device comprises a housing which forms a housing front face therein. The housing has in the housing front face an outlet for the components. The device further comprises a piston having a piston front face. The piston is arranged within the housing such that the piston front face and the housing front face are facing each other.

The device is adapted such that the piston is movable within the housing for positioning the piston front face and the housing front face toward each other.

The piston front face and the housing front face are adapted, in particular may be shaped, to form a channel for the components between each other at least in contact of the piston front face and the housing front face.

The device is adapted to reduce the channel upon urging the piston front face and the housing front face against each other and thereby to displace the components to flow toward the outlet. In one embodiment the device is adapted such that a reduction or compression of the channel causes the component or components to be displaced and to flow along the channel. Preferably the device is adapted such that the flow of the component(s) is directed toward the outlet.

The invention is advantageous in that it provides for a device which is relatively inexpensive and easy to use. The device of the invention may further be reusable although the device is adapted for mixing individual components. In particular the invention may not require a mixing element to be exchanged for multiple uses. Further the invention is advantageous in that it provides a relatively compact device. For example a long mixing tip may not be required. Further the device helps minimizing any residual material or components in the device after use. This is because the device preferably allows for substantially emptying any structure or structures which provide for mixing of the components. In particular the device may be adapted such that the structure which forms the channel, or a part of the channel, is compressed upon urging the piston front face against the housing front face. Further even small quantities may be provided at minimized efforts and costs with the device of the present invention due to the relatively inexpensive configuration and minimized residual material.

In one embodiment the channel is reduced or reducible by reduction (for example compression) of a channel cross-section. The channel cross section thereby is defined in a plane perpendicular to a path along which the channel extends. For example the channel may extend at a generally uniform cross-section. Further the channel may be reduced by compression of at least a portion of the piston, in particular a portion forming the channel.

In one embodiment the channel extends at least over a part of its length substantially spirally or helically at the piston front face. Accordingly the path along which the channel extends may correspond to spiral or helix.

In a further embodiment the piston is deformable at least adjacent the piston front face. In particular portions of the piston which form the channel, or part of the channel, may be deformable or compressible.

In one embodiment the channel is at least partially formed by a structure within the piston front face. The structure may be an open groove within the piston front face. This open groove may be closed in contact with the housing front face so that a closed channel is formed in contact of the housing front face and the piston front face. The groove may for example be open along a section or the entire length of the groove.

In another embodiment the channel is formed by a tube which is arranged at the piston front face. The tube thus preferably forms a closed channel, for example in a contact and in a non-contact relationship between the housing front face and the piston front face. The tube is preferably laterally deformable. This means in at least one dimension perpendicular to the path along which the tube extends the tube may be deformable, in particular compressible.

In a further embodiment the device contains a quantity of components to be mixed and dispensed. Such a quantity preferably includes a total of sub-quantities of individual components, for example the total of a first sub-quantity of a first component and a second sub-quantity of a second component.

In one embodiment the channel is adapted to contain substantially the entire quantity of the components or all components receivable or present in the device. Thus the dispensation of unmixed amounts of components is preferably minimized.

In one embodiment the device has a first inlet for at least one of the components, wherein the first inlet is arranged such that the at least one component can be provided between the piston front face and the housing front face. The first inlet may be formed by a passageway formed between the piston and the housing. Further the first inlet may be formed by a passageway through the piston.

In a further embodiment the device has a second inlet for at least one of the components. Preferably the second inlet is arranged such that the component can be provided between the piston front face and the housing front face. Again the second inlet may be formed by a passageway formed between the piston and the housing and/or through the piston. Further the first and second inlets may be arranged at substantially opposite sides of the piston.

In a preferred embodiment the piston front face and the housing front face each are conically shaped. The piston is preferably arranged within the housing such that the apexes of the cones are oriented in the same direction. The cone of the housing is preferably an inner cone (or a concave cone) and the cone of the piston is preferably an outer cone (or a convex cone). Further the outer and inner cones may have different cone angles.

In one embodiment the cone angles are selected such that, with the piston being appropriately arranged within the housing, the peripheries of the piston front face and the housing front face are closer relative to each other than the cone apexes of the piston front face and the housing front face. An appropriate arrangement of the piston within the housing corresponds to the piston front face cone and the housing front face cone being oriented in the same direction, for example with the apexes pointing into the same direction.

In one embodiment the piston is made of an elastic material, for example made of rubber or thermoplastic elastomer. Further the channel preferably has a cross-section perpendicular to the path the channel extends having an area of about $0.05$ mm$^2$ to $10$ mm$^2$ Further the channel preferably has two open ends at the beginning and the end of the path along which it extends. The channel may for example extend spirally, helically or may extend along another path providing two open ends. The channel may particularly not extend along a closed path, for example not along a closed circle.

In a further embodiment the device has a plunger which is movable independently from the piston. Such a device is preferably adapted such that at least one of the components, for example a first component, can be accommodated in a (preferably generally liquid tight) space left between the plunger and the piston. Further such a device may be adapted such that a movement of the plunger toward the piston causes the first component to flow though the first inlet and/or the second inlet and a further movement of the plunger preferably causes the piston to move toward the housing front face. In particular the plunger and the piston may be arranged within the housing such that the plunger is operable to push the piston forward in a direction toward the housing front face. Accordingly a movement of the plunger preferably initially causes the first component to be transferred from a space between the plunger and the piston to a space between the piston front face and the housing front face. And such movement preferably subsequently causes the first component to be transferred from the space between the piston front face and the housing front face through the outlet out of the device. A second component may be accommodated (preferably separated from a first component) initially within the space between the plunger and the piston. Thus the two components may be transferred from the space between the plunger and the piston to the space between the piston front face and the housing front face simultaneously. Further a second or third component may be accommodated initially within the space between the piston front face and the housing front face. Such a component may be in the form of a liquid or a powder, for example. A powdery component may for example be coated on the piston front face. This powdery component may be adapted to solve in the first component and optionally the first and second components initially present between the plunger and the piston.

In one embodiment the device comprises a dental material, preferably a liquid dental material. Such a material may be selected from adhesives, bondings, liners, sealants, caries detectors, caries indicators and caries removing agents, for example.

DETAILED DESCRIPTION OF THE INVENTION

Figure 1:
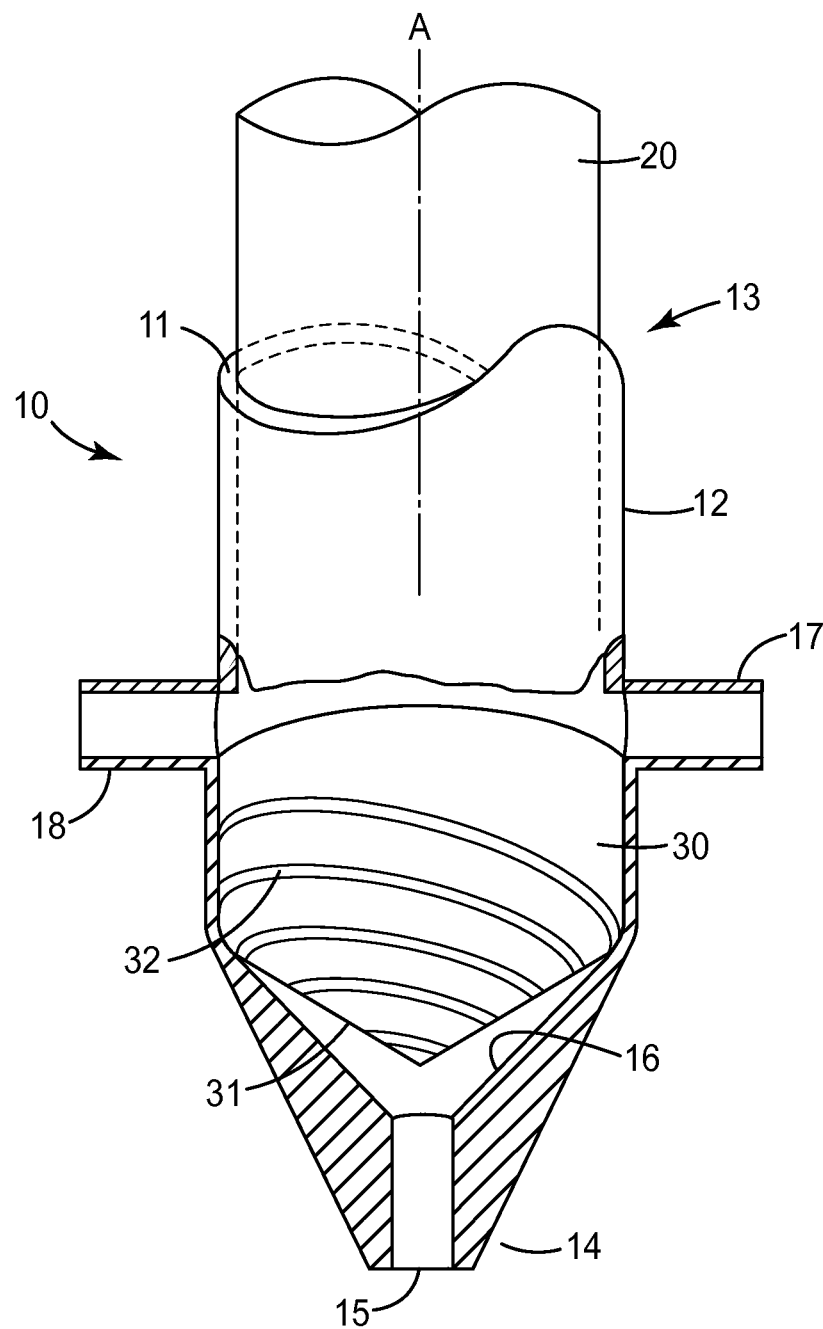
FIG. 1 is a perspective view of a device for mixing and dispensing two flowable components according to an embodiment of the invention.

FIG. 1 shows a device 10 for mixing and dispensing at least two flowable components. The device comprises a housing 11 which extends along a longitudinal axis A of the device 10. The housing 11 has a tubular section 12 along the longitudinal axis A. The tubular section 12 in the example extends with a generally uniform ring shaped profile. However the person skilled in the art will recognize other suitable shapes for the tubular section, for example a profile having a common generally circular or elliptical periphery and two circular, elliptical or D-shaped recesses. The housing 11 has an open rear end 13 (not illustrated in detail) within which a plunger 20 is received. The plunger 20 is preferably movable at least with one end within the tubular section 12 of the housing 11. Further the housing 11 has a front end 14 which has an outlet 15 for the components. The housing 11 at the front end 14 forms a front face 16 in the inside of the housing 11. The front face 16 forms an opening into the outlet 15. A piston 30 is arranged within the housing 11, in particular within the tubular section 12. The piston 30 has a front face 31 and is arranged within the housing such that the piston front face 31 and the housing front face 16 are facing each other. The piston 30 is movable within the housing 11 for positioning the piston front face 31 and the housing front face 16 toward each other. In the example shown the piston 31 is positioned relative to the housing front face 16 such that the piston 31 is in contact with the housing front face 16. The piston front face 31 forms an open channel 32. The open channel 32 is adapted to receive the components to be mixed. The components to be mixed may be provided in a space between the piston front face 31 and the housing front face 16, for example in a situation in which the piston 30 is retracted further toward the rear end 13 relative to the position shown in the Figure. Therefore the device 10 has a first inlet 17 and a second inlet 18. The first inlet 17 and the second inlet 18 are arranged at opposite sides of the housing 11. Thus components provided into the housing preferably arrange substantially side by side within the space left between the piston front face 31 and the housing front face 16. The device 10 so filled with the components may be operated by pushing the plunger and thereby urging the piston 30 toward the front end 14 of the housing 11. Upon the piston front face 31 reaching the housing front face 16 further pushing preferably causes the piston to deform and thereby to reduce the channel 32 in cross-section. This causes on the one hand the components to be squeezed out of the channel 32 and one the other hand to flow along the channel 32. Accordingly components being squeezed out of the channel 32 are caused to flow in a first flow stream substantially radially to the longitudinal axis A toward the outlet 15, whereas the channel 32 guides the components present therein in a second flow stream approximately laterally to the radially flowing components. In response of a successive reduction the channel 32 the components accordingly are successively divided in the first flow stream and the second flow stream which in continuously cross and merge on the way toward the outlet. Thereby a mixing and dispensing of the components is achieved.

In the example the piston front face 31 has a generally conical shape. Further a groove extends helically into the piston front face 31 and forms the channel 32. The housing front face 16 also has a conical shape, however the cone of the housing front face 16 is steeper that the cone of the piston front face 31. Therefore upon pushing the piston 30 toward the front end 14 of the housing 11 causes the piston to successively deform from its periphery toward its center. This is because upon pushing the piston 30 toward the front end 14 of the housing 11 the piston front face 31 touches the housing front face 16 at the outer periphery first, and only further pushing the piston causes the piston front face 31 to successively conform to the housing front face 16.

The piston 30 is preferably made of a resilient material, for example a rubber or thermoplastic elastomer.

Figure 2:
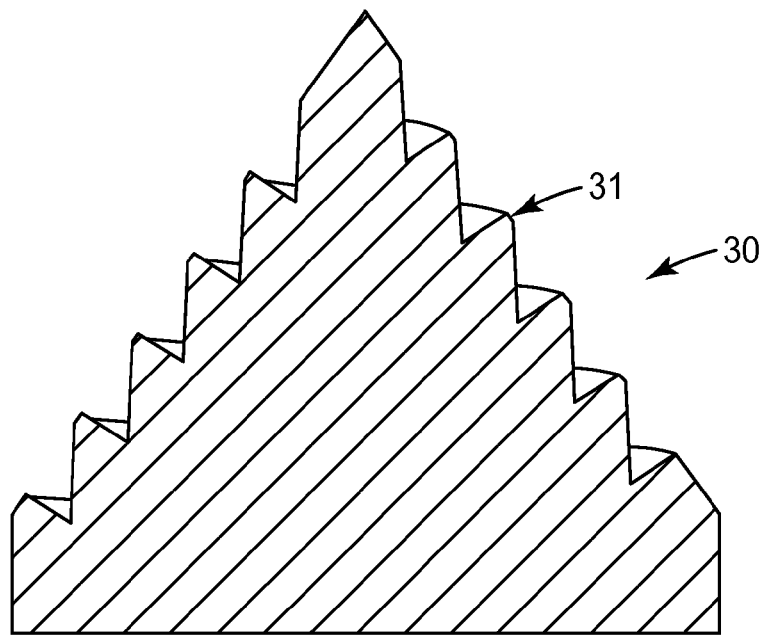
FIG. 2 is a cross-sectional view of a piston according to one embodiment of the invention.

FIG. 2 shows the piston 30 in more detail. The piston front face 31 has an overall generally conical shape and a channel 32 extending helically over the piston front face 31 between the apex of the cone and the periphery of the cone. The channel 32 accordingly extends along a conical helix. The channel 32 is formed by a generally V-shaped groove. However other shapes, in particular a U-shape, are possible. The cross-section and length of the channel 32 are preferably selected such that a predetermined amount of components can be received within the channel without substantially flowing outside the general cone shape of the piston front face 32. Thus in the device filled with the predetermined amount of components generally the entire amount matches with the channel. This helps avoiding unmixed components to be dispensed from the device because generally the entire amount of components are forced undergo a dividing and merging of flow streams within and outside the channel 32.

Figure 3:
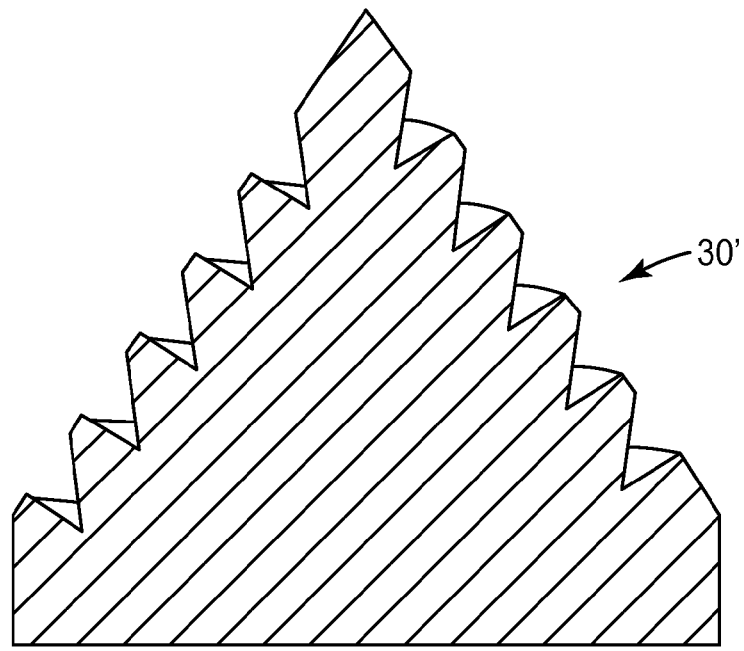
FIG. 3 is a cross-sectional view of a piston according to a further embodiment of the invention.

FIG. 3 shows a further piston 30' having deeper grooves having a greater capacity for the components. This means that the grooves are shaped to store a larger quantity of the components. Accordingly the device of the invention may be easily adapted to different quantities of components to be mixed by exchange of the piston.

Figure 4:
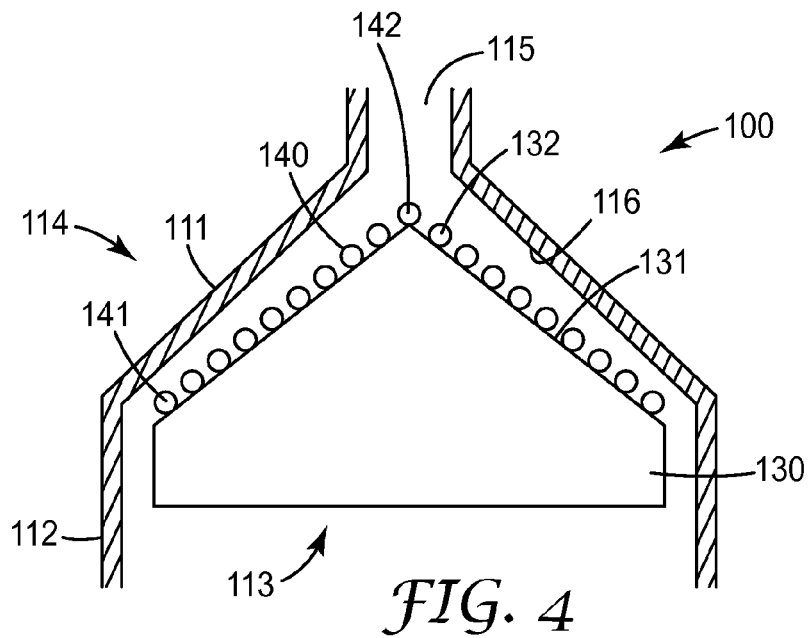
FIG. 4 is a cross-sectional view of a device for mixing and dispensing two flowable components according to a further embodiment of the invention.

FIG. 4 shows an alternative device 100 for mixing and dispensing at least two flowable components. The device 100 comprises a housing 111 which has a tubular section 112. The housing 111 may be technically identical to the housing of the example in FIGS. 1 to 3. In particular the housing 111 has an open rear end 113 (not illustrated in detail) for receiving a plunger (not illustrated). Further the housing 111 has a front end 114 which has an outlet 115 for the components. The housing 111 at the front end 114 forms a front face 116 in the inside of the housing 111. The front face 116 forms an opening into the outlet 115. A piston 130 is arranged within the housing 111, in particular within the tubular section 112. The piston 130 has a front face 131 and is arranged within the housing such that the piston front face 131 and the housing front face 116 are facing each other. The piston 130 is movable within the housing 111 for positioning the piston front face 131 and the housing front face 116 toward each other. Between the piston front face 131 and the front face 116 a tube 140 is arranged spirally disposed over at least part of the area of the front face 116. The tube 140 forms a channel 132 to receive the components to be mixed. The components to be mixed may be supplied side-by-side into the tube 140. The device 100 so filled with the components may be operated by pushing the plunger 130 and thereby urging the piston 130 toward the front face 116 of the housing 111. Upon the piston front face 131 reaching the housing front face 116 further pushing preferably causes the tube to get compressed between the front face 131 and the housing front face 116. Thereby the channel 132 reduces in cross-section and causes the components to be squeezed out of the tube 140. Thus the components are dispensed from the outlet 115. It has been found that certain flowable and mixable components, although provided as individual components into the tube exit the tube as a mixture.

In the example the piston front face 131 as well as the housing front face 116 have a generally conical shape. The cone of the housing front face 116 is however steeper that the cone of the piston front face 131. Therefore upon pushing the piston 130 toward the front face 116 of the housing 111 causes the tube 140 to successively deform from a first end 141 of the tube 140 which is arranged adjacent the housing 111 toward a second end 142 of the tube which is arranged at the outlet 115. Thus the tube 140 is preferably successively emptied from the first end 141 toward the second end 142 of the tube 140. Thus the components are preferably urged to flow in a direction toward the outlet 115 and prevented from flowing in an opposite direction.

Figure 5:
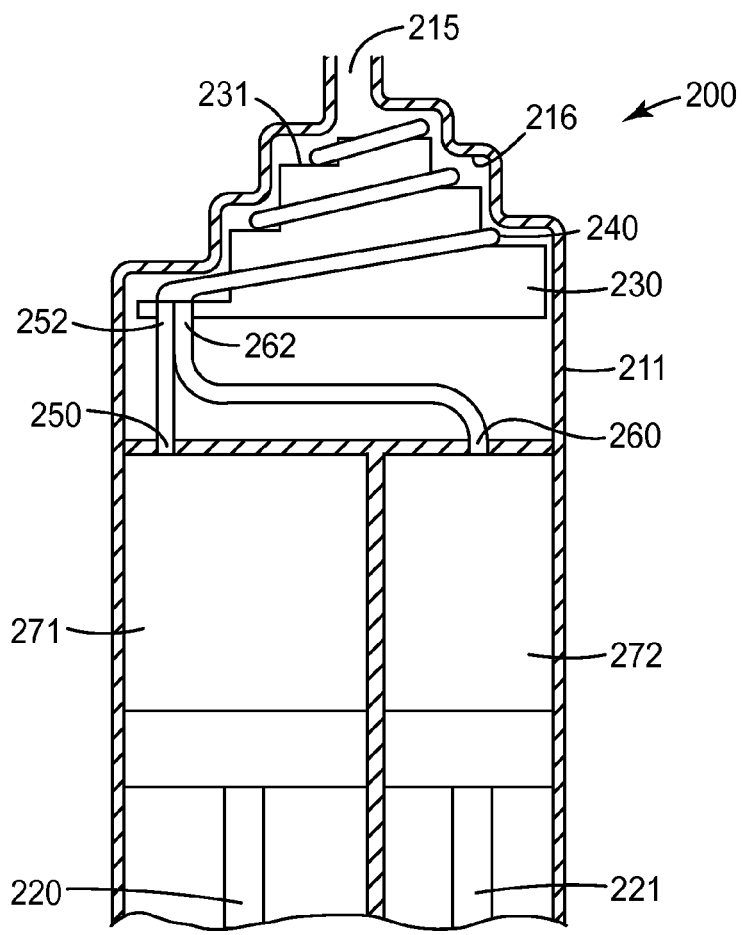
FIG. 5 is a cross-sectional view of a device for mixing and dispensing two flowable components according to still a further embodiment of the invention.

FIG. 5 shows an alternative device 200 which is identical to the example shown in FIG. 4 except for the housing 211 having a stepped helical front face 216 and the piston 230 having a corresponding stepped helical front face 231. A tube 240 is arranged between the piston front face 231 and the housing front face 216. The example shows in further detail inlets 250, 260 which at first ends 251, 261, respectively, are connected to first and second containers 271, 272. Each of the first container 271 and the second container 272 contains a component of a dental material. The device 200 further has a first plunger 220 and a second plunger 221 for extruding the respective component in the first and second container 271, 272 into the inlets 250, 260. The inlets 250, 260 are connected to the tube 240 at their second ends 252, 262, respectively. Upon simultaneously moving the plungers 220, 221 toward the containers 271, 272, the components are supplied into the tube 240 in a side-by-side arrangement via the inlets 250, 260. The so filled tube 240 may be subsequently squeezed by movement of the piston 230 toward the housing front face 216 whereby the components are urged toward outlet 215. The components are preferably prevented from flowing away from the outlet 215 by the plungers 220, 221 blocking the components from flowing back into the containers 271, 272.

The invention claimed is:

1. A device for mixing and dispensing at least two flowable components which are adapted to be mixed to form a dental material, the device comprising:
   a housing forming a housing front face therein,
   the housing having in the housing front face an outlet for the components; and a piston having an piston front face and being arranged within the housing such that the piston front face and the housing front face are facing each other;

the device being adapted such that the piston is movable within the housing for positioning the piston front face and the housing front face toward each other;

wherein the piston front face and the housing front face are adapted to form a channel for the components between each other at least in contact of the piston front face and the housing front face, wherein the channel is formed by a laterally deformable tube arranged at the piston front face; and wherein the device is adapted to compress the channel upon urging the piston front face and the housing front face against each other and thereby to displace the components to flow toward the outlet.

2. The device of claim 1, wherein the channel extends at least over a part of its length substantially spirally or helically at the piston front face.

3. The device of claim 1, wherein the piston is deformable at least adjacent the piston front face.

4. The device of claim 1, further comprising a quantity of components to be mixed and dispensed, wherein the channel is adapted to contain substantially the entire quantity.

5. The device of claim 1, further comprising a first inlet for at least one of the components, wherein the first inlet is arranged such that the at least one component can be provided between the piston front face and the housing front face.

6. The device of claim 5, wherein the first inlet is formed by a passageway between the piston and the housing and/or through the piston.

7. The device of claim 5, having a second inlet for at least one of the components, wherein the second inlet is arranged such that the component can be provided between the piston front face and the housing front face.

8. The device of claim 7, wherein the second inlet is formed by a passageway between the piston and the housing and/or through the piston, and wherein the first and second inlets are arranged at substantially opposite sides of the piston.

9. The device of claim 1, wherein the piston front face and the housing front face are conically shaped with the apexes cones being oriented in the same direction.

10. The device of claim 9, wherein the cone of the housing is an inner cone and the cone of the piston is an outer cone, the outer and inner cones having different cone angles.

11. The device of claim 10, wherein the cone angles are selected such that the peripheries of the piston front face and the housing front face are closer relative to each other than the cone apexes of the piston front face and the housing front face.

\* \* \* \* \*